US006090614A

United States Patent [19]

Golenda

[11] Patent Number: 6,090,614

[45] Date of Patent: Jul. 18, 2000

[54] METHOD FOR PRODUCTION OF PLASMODIUM CAUSING RELAPSING MALARIA

[75] Inventor: Claudia Golenda, Germantown, Md.

[73] Assignee: The United States of America as represented by the Secretary of the Army, Washington, D.C.

[21] Appl. No.: 08/694,384

[22] Filed: Aug. 8, 1996

[51] Int. Cl.[7] ........................................ C12N 1/10

[52] U.S. Cl. ........................................ 435/258.2

[58] Field of Search ........................................ 435/258.2

[56] References Cited

U.S. PATENT DOCUMENTS 4,681,899 7/1987 Ohnishi .................................. 514/602

OTHER PUBLICATIONS

Renapurkar et al., IRCS. Med Sci., vol. 11(1), p. 7–8, 1983.

Mons et al., Exp. Parasitol., vol. 66(2), p. 183–188, 1988.

Zhou et al., Chinese J. Parasitology & Parasitic Diseases, vol. 9(4), p. 258–60, 1991.

*Primary Examiner*—Chhaya D. Sayala

*Attorney, Agent, or Firm*—John Francis Moran; Charles H. Harris

[57] ABSTRACT

This invention provides for recycling parasites and maintaining long-term cultures of *P. vivax* and *P. ovale*. Preferred conditions include 1) the immediate transfer of parasites to human reticulocytes during the first and second in vitro culture cycles, 2) the use of McCoy's 5A medium modified with L-glutamine containing 25 mM HEPES buffer supplemented with 20% human AB serum, 3) the continual addition of reticulocytes to the culture every 34–44 hours after the beginning of a new culture cycle, and 4) the use of alternate static (growth and differentiation phase) and shaker (invasion phase) culture.

1 Claim, No Drawings

METHOD FOR PRODUCTION OF PLASMODIUM CAUSING RELAPSING MALARIA

FIELD OF THE INVENTION

This invention relates to a process for growing *Plasmodium vivax* by in vitro cultivation. The parasites are obtained from a nonhuman primate host and grown in culture containing enriched primate reticulocytes.

BACKGROUND OF THE INVENTION

*Plasmodium vivax* is the most common malaria parasite affecting humans, comprising 56% of all human malaria cases reported in 1992, excluding Africa. In India, *P. vivax* is the primary cause of malaria. It is the predominant species found in temperate climates, but also occurs in large areas of the tropics, excluding Africa. Because the majority of Africans lack the Duffy blood group antigens, they are not susceptible to *P. vivax*. In Africa, *P. ovale* replaces *P. vivax*, occurring commonly only in areas populated by Duffy antigen negative individuals who are not susceptible to *P. vivax*. *P. vivax* and *P. ovale* are classified as benign tertian human malarias and share many similarities, including ability to infect nonhuman primates. Although the disease caused by *P. vivax* is seldom the sole cause of fatalities, it causes a severe, acute illness and, unlike *P. falciparum*, results in relapsing episodes of disease months or years after the original infection. Successful therapy requires clearance of both the blood and liver stages. Chloroquine-resistant *P. vivax* has been recently confirmed in Southeast Asia. A serious impediment to drug and vaccine development has been the inability to culture the parasites, which preferentially invade reticulocytes.

There has not previously been a standardized process for long-term cultivation of *P. vivax* in vitro. Mons, et al. (Parasitol. 66: 183–188 (1988)) disclosed a method for culture in infected monkey blood in a shaker culture for 5–6 cycles by adding reticulocytes obtained from bleeding monkeys that were treated with the hemolytic drug phenylhydrazine hydrochloride. Lanners (Parasit Res. 78:699–701)) reported maintaining parasites up to 20 days in a flow vessel in which human reticulocyte fractions (Percoll Renograffin gradient preparations) were added irregularly (at days 4, 9 and 13) to parasites originating from monkeys. The data indicates lack of continued recycling of parasites, since only one unhealthy trophozoite was seen at 20 days. Both procedures used RPMI 1640 medium supplemented with either 15% or 20% human serum. Neither procedure used alternate static and agitation phases during culturing. Both of the articles report that monkey parasitized cells became extremely fragile and ruptured before differentiation to the mature schizont stage.

SUMMARY OF THE INVENTION

The present invention is a method for growing species of Plasmodium which cause relapsing malaria which comprises the steps of:

1) collecting infected blood containing white blood cells from primates when parasitemia is at least 0.1%,
2) removing at least 90% of the white blood cells before initiating the culture,
3) resuspending the parasitized cells in culture medium containing serum and transferring the resulting suspension to culture dishes or flasks,
4) incubating the culture of step 3 in a static culture, 5) transferring the product of step 4 to a centrifuge tube and centrifuging to pelletize the parasitized cells,
6) aspirating the medium above the pellet without disturbing the pellet,
7) adding enriched reticulocytes to the parasitized cells with mixing followed by addition of sufficient medium to provide suspension having a hematocrit of at least 10%,
8) Transferring the suspension obtained in step 7 to culture flasks or dishes, gassing, covering, then shaking the vessel until rings and/or trophozoites predominate in the cell suspension with invasion of the reticulocytes,
9) centrifuging the product of step 8, then adding fresh medium to the infected cells in sufficient amount to provide a medium with hematocrit of not more than 10%, and
10) repeating steps 4–9 every 1–2 days to continually recycle parasites in culture.

DESCRIPTION OF THE INVENTION

No method for continuous culturing of *P. vivax* or *P. ovale* is known. The three major problems in establishing long-term in vitro cultivation of *P. vivax* are 1) the need for a constant source of enriched human reticulocytes for continuous cycling of the parasites, 2) need to provide conditions which enhance the invasion of reticulocytes by the parasite and 3) the need to reduce the fragility of parasites in culture so that maturation of parasites to schizonts containing healthy merozoites occurs.

It is the purpose of this invention to provide means for long-term cultivation of *P. vivax* parasites. The possibility of culturing *P. vivax* long-term with recycling in vitro makes it possible to evaluate effect of drugs on a given population of parasites for purposes of drug screening and for treatment. The method of the invention also provides means for producing parasite antigens for development of vaccines, and for evaluating effect of antibodies raised to potential vaccines. By methods of the invention it is possible to reduce fragility of parasites in culture so that maturation of parasites to schizonts containing healthy merozoites (the invasion stage of the parasite) occurs. Hence, it is possible to more nearly replicate in vitro the growth of the parasites in the host animal.

It is possible, for purposes of the practice of this invention, to utilize blood from the therapeutic bleeding of patients with conditions such as hemochromatosis and polycythemia. Such blood is usually discarded as biological waste. Blood from such sources contains an increased concentration of reticulocytes. This blood may be further enriched to obtain higher percentages of reticulocytes for use in methods of the invention for cultivation of *P. vivax*.

Preferred conditions which include 1) the immediate transfer of parasites to primate reticulocytes during the first and second in vitro culture cycles 2) the use of McCoy's 5A medium modified with L-glutamine containing 25 mM HEPES buffer supplemented with 20% human AB serum, 3) the continual addition of reticulocytes to the culture every 34–40 hours after the beginning of a new culture cycle, and 4) the use of alternate static (growth and differentiation phase) and shaker (invasion phase) culture, are disclosed herein. Moreover, the use of blood from patients who are bled frequently for therapeutic reasons provides an economical, continuing source of blood for purposes of providing enriched reticulocytes used in the method of the invention.

The factors which promote invasion of the human reticulocytes by *P. vivax* parasites are 1) use of enriched human reticulocytes obtained from blood of Duffy antigen-positive primates, 2) addition of reticulocytes to the cultures at regular intervals (every 1–2 days) accompanied by shaking of the culture (hematocrit is increased at least 2 times that used during the growth phase in static culture), and 3) co-culturing the parasites with primate reticulocytes at the end of the first growth cycle.

The reticulocyte enrichment by differential centrifugation, as disclosed herein, in homologous plasma (plasma from the same individual as the source of the reticulocytes) is particularly useful for maintaining the homeostasis of cell membranes during the enrichment procedure. Conversely, the use of chemical gradients (for example, Percoll, Renograffin, Ficoll and Nycodenz) may impair the integrity of the cell surface by modifying receptors or causing cell fragility. Limited invasion of reticulocytes by parasites and/or rupture of parasitized cells before maturation to schizonts often occurs in reticulocytes enriched using such chemical gradients. The percentage of reticulocytes in plasma-enriched fractions used in the process of this invention was about 15% to 20%. However, the parasite invasion using the inventive procedure was higher than that found using reticulocytes obtained using a Percoll Renograffin gradient even with elevation of reticulocytes to as high as 70%, as disclosed in the prior art.

Materials and Methods

Enrichment of Reticulocytes

Reticulocytes were separated from the peripheral blood of patients undergoing therapy for hemochromatosis or polycythemia. Duffy antigen-positive therapeutic blood containing at least 2% reticulocytes was used. White blood cells were removed from the whole blood using a leukocyte separation filter (SEPACELL™, Baxter Healthcare Corporation, Fenwal Division, Deerfield, Ill.) following the manufacturer's instructions. The filtered blood was then transferred to eight to ten 50-ml sterile conical centrifuge tubes and centrifuged at 1000×g for 15 minutes at room temperature. The volume of the packed cells was recorded. Excess plasma was removed from each tube to achieve about a 1:5 ratio of plasma:packed cells, resulting in a hematocrit of about 80% to 85%. Excess plasma was stored at 5° C. and used for a second centrifugation step (described below). Nine (9) ml of the 80% to 85% hematocrit blood was then transferred to eight 10 ml Oak Ridge centrifuge tubes (Nalgene, Rochester, N.Y.) and placed in a 37° C. water bath for 75–90 minutes. The tubes were then centrifuged using a version of Murphy's procedure (Murphy, J. J., Lab. Clin. Med. 83:334 (1973)). Tubes were centrifuged at 35,000×g for 30 minutes at 30°–32° C. The plasma was then aspirated to approximately 0.25 inch above the top of the cell pellet. The remaining plasma and about 25% of the upper cell pellet (approximately 2.2 ml) were removed from the tubes and pooled. This suspension of pooled pellets was diluted with an equal volume of fresh, homologous plasma (50% hematocrit) and 8 ml aliquots were deposited into 10-ml Oak Ridge tubes. The 37° C. incubation, centrifugation and aspiration procedures were repeated on the resulting suspension to produce enriched reticulocytes. However, this time, only the top 10% of the final pellets are collected, then pooled to obtain approximately 2.0 ml of enriched reticulocytes. The reticulocytes were washed with 10 ml of McCoy's 5A medium modified with L-glutamine-containing 25 mM HEPES buffer (Gibco BRL, Gaithersburg, Md.), centrifuged at 1000×g for 10 minutes at room temperature. All but 1 ml of the supernatant medium was removed. The washing step was repeated after which the resulting cell pellet was stored at 4° C for up to 2 weeks. (Alternatively, washed reticulocytes can be cryopreserved in Glycerolyte[R] (Baxter Healthcare Corporation, Fenwall Division, Deerfield, Ill.).) This suspension is used for periodic addition to cultures to assure recycling of parasites. The first and second centrifugation increases the percentage of reticulocytes 2 to 5 times. The final percentage of reticulocytes depends on the percent of reticulocytes in the initial unit of therapeutic blood.

Collection of Parasites for Culture and Initiation of Static Cultures

Susceptible monkeys may be infected with I.V. injection with either fresh or frozen *P vivax*-infected blood. (Alternatively, the blood may be obtained from infected primates.) The development of blood parasites was monitored by examining thick and thin Geimsa-stained slides every two days. Blood was collected for in vitro culturing when the parasitemia reached at least 0.1% and 70% of the parasites were rings or young trophozoites. The infected blood was collected into a vacutainer tube (Becton Dickenson Vacutainer Systems, Rutherford, N.J.) containing citrate phosphate dextrose adenine anticoagulant solution (0.15 ml for every 0.5 ml of blood collected), diluted 1:5 with McCoy's modified medium and eluted under gas pressure (5% $CO_2$, 5% $O_2$, 90% $N_2$) through a loosely packed CF 11 cellulose powder column pre-wetted with medium according to the method of William and Richards (*Annals of Trop. Med. and Parasitol.,* 67:169 (1973)). The effluent was collected in a sterile centrifuge tube. The column was then washed with 0.5 ml of McCoy's medium while the gas flow was permitted to continue until bubbles appeared at the bottom of the column. The effluent was then centrifuged at 500×g for 10 minutes at room temperature. The cell pellet was first washed in McCoy's medium, then washed in McCoy's medium supplemented with 20% AB+ serum. Thick and thin GEISMA-stained blood films were examined to confirm that at least 70% of the infected cells contained rings or young trophozoite-stage parasites. The resultant volume of the cell pellet, divided by 6%, was used to determine the amount of cell suspension to be used for in vitro culturing. For example, for 0.2 ml of pelleted cells, the total volume available for culturing will be 0.2/0.06=3.33 ml.) The difference between the volume of the pellet and the total culture suspension volume (3.33–0.2) indicates the amount of McCoy's medium containing 20% AB+ serum that must be added to achieve the final suspension volume.

Static cultures are initiated by adding 500 $\mu l$ of the suspension to the wells of 4-well Nunclon[R] multi-dish culture plates (NUNC, Denmark) which were incubated in a candle jar environment by the method of Trager and Jensen (*Science* 193:673 (1976)). Parasite differentiation was monitored by observation of Geimsa-stained thick and thin films at 8–12, 20–24 and 34–38 hours. Additionally, the number of parasites was determined in 1.0 thick films. After 20–24 hours, the culture medium was changed without disturbing the layer of parasitized red cells. If, after 34 hours, 50% of the parasites had begun the schizongy stage (2–4 nuclei) the shaker phase (described below) was initiated. If not, slides were made very 2–3 hours until schizongy was observed, after which the shaker phase was initiated.

Passage of Parasites to Human Reticulocyte Preparations

Parasitized cells were transferred to a 15-ml sterile, conical tube and centrifuged at 500×g for 10 minutes at room temperature. The medium was aspirated to a level of 0.25 inch above the top of the pellet. Pre-warmed reticulocytes (37° C. for 15 minutes, prepared as described above) were mixed with the pellet of parasitized cells to provide 1–3× the volume of reticulocytes compared to the parasitized cells. The combined volume was recorded and fresh McCoy's medium containing 20% AB+ serum was added to obtain a hematocrit of 12%–15%. The suspension was transferred to a type T tissue culture flask (Bellco Glass, Inc, Vineland, N.J.), gassed for 15 seconds (5% $CO_2$ 5% $O_2$, 90% $N_2$) and shaken at 100 cycles per minute at 37° C. for 10–14 hours. The contents of the culture flask (9 $cm^2$ growth area) were transferred to a sterile, conical tube, centrifuged (500×g for 10 minutes at room temperature), the supernatant was removed and thick and thin Geimsa stained slides were made from the resulting pellet. Slides were examined for presence of rings and/or young trophozoite stage parasites on thick and thin Geimsa-stained films for slides to verify that parasites had invaded the reticulocytes. If there were more schizonts present than rings, the culture was left on the shaker for an additional 2–4 hours until rings predominated. Fresh medium was added to the pellet to bring the hematocrit to 6%. Aliquots (500 $\mu$l) of the suspension were added to each well and the plates were incubated in a candle jar environment in accord with the teachings above.

Every 34 to 38 hours the cultures were maintained by adding enriched reticulocyte preparations to provide fresh target cells for the parasites. This addition increased the volume of the parasitized cells at least 1 fold with each parasite cycle, resulting in the need for larger culture vessels. After the third cycle, the static phase was maintained in 35 $cm^2$ vented culture flasks that held up to 6 ml of a 6% hematocrit suspension. A larger volume type T tissue culture flask (15–30 $cm^2$ growth area) may also be used during the shaker phase.

The preferred timing of adding the reticulocytes to the culture when parasites developed to schizonts and shifting from static to shaker culture as taught herein proved highly beneficial. Likewise, co-culturing reticulocytes and parasites at a hematocrit 2 times that of the static culture in order to allow greater contact between parasitized cells and target reticulocytes also proved to be highly advantageous and allowed the continued recycling of the parasites.

The method described in here is repeated using blood infected with *P. ovale*. The primary difference is that, Duffy antigen negative blood is used for this study. Since blood of most Africans is Duffy antigen negative, the therapeutic blood from which the reticulocytes and homologous plasma are to be obtained should be sought among persons of African descent who have Duffy antigen negative blood.

What is claimed is:

1. A method of growing species of *Plasmodium vivax* or *ovale* comprising the steps of:

1) collecting infected blood containing white blood cells from infected blood of primates when parasitemia is at least 0.1%, 2) removing at least 90% of the white blood cells before initiating the culture, 3) resuspending the parasitized cells in culture medium containing serum and transferring the resulting suspension to culture dishes or flasks, 4) incubating the culture of step 3 in a static culture, 5) transferring the product of step 4 to a centrifuge tube and centrifuging to pelletize the parasitized cells in said product, 6) aspirating the medium above the pellet without disturbing the pellet, 7) adding enriched reticulocytes to the parasitized cells obtained in step 6 with mixing followed by addition of sufficient medium to provide suspension having a hematocrit of at least 10%, 8) transferring the suspension obtained in step 7 to culture in vessels, gassing, covering, then shaking said vessels until rings and/or trophozoites predominate in the cell suspension with invasion of the reticulocytes, 9) centrifuging the product of step 8, then adding fresh culture medium to the infected cells in sufficient amount to provide a medium with hematocrit of not more than 10%, and 10) repeating steps 4–9 every 1–2 days to continually recycle parasites in culture.

* * * * *